US006187400B1

(12) United States Patent
Woo et al.

(10) Patent No.: US 6,187,400 B1
(45) Date of Patent: Feb. 13, 2001

(54) MEDICAL TUBING AND PUMP PERFORMANCE ENHANCEMENT BY IONIZING RADIATION DURING STERILIZATION

(75) Inventors: Lecon Woo, Libertyville; Michael T. K. Ling, Vernon Hills; Chuan Qin, Gurnee; Birendra K. Lal, Lake Zurich; Yuan-pang S. Ding, Vernon Hills; Donna L. Rostron, Bartlett, all of IL (US); Susan R. Mizener, Walworth, WI (US); Patrick T. Ryan, Crystal Lake, IL (US)

(73) Assignee: Baxter International Inc., Deerfield, IL (US)

( * ) Notice: Under 35 U.S.C. 154(b), the term of this patent shall be extended for 0 days.

(21) Appl. No.: 09/084,816

(22) Filed: May 26, 1998

Related U.S. Application Data (63) Continuation-in-part of application No. 08/642,275, filed on May 3, 1996, now Pat. No. 5,932,307.

(51) Int. Cl.[7] .............................. A61M 1/00; B32B 31/28; B29D 22/00

(52) U.S. Cl. ...................... 428/36.6; 428/36.7; 428/36.9; 428/36.91; 138/137; 138/141; 604/93.01; 604/151; 156/272.2; 156/244.13

(58) Field of Search .............................. 428/36.9, 36.91, 428/36.6, 36.7; 138/137, 141; 604/403, 408, 93.01, 131, 151, 264, 6.11, 6.16; 156/272.2, 244.13, 244.17, 244.24

(56) References Cited

U.S. PATENT DOCUMENTS 813,918   12/1906   Schmitz .

(List continued on next page.)

FOREIGN PATENT DOCUMENTS 250874    8/1988   (CS) .
1 928 843  6/1969   (DE) .

(List continued on next page.)

OTHER PUBLICATIONS

Wilpers, et al., Functionalized Modified High Melt Flow Polyolefins, United States Statutory Invention Registration No. H1419, Feb. 7, 1995.
The Effect of Plastic Formulation Variables on Bond Strengths Achieved With Typical Medical Device Adhesives, presented at Manufacturing Medical Plastics '95 by Pat Courtney, Senior Application Engineer, Loctite Corporation.
Courtney, P., et al., Adhesive Bonding of Medical Plastics: An Overview, Medical Plastics and Biomaterials, Jan./Feb., 1996, pp. 20–25.
Medical Tubes Use Metallocene Resin, European Plastic News, Jun., 1996, p. 17.
Extrusion Line for Medical Tubes, Industrial & Production Engineering (PE), Dec., 1988, p. 17.

*Primary Examiner*—Rena L. Dye
(74) *Attorney, Agent, or Firm*—Mark J. Buonaiuto; Joseph A. Fuchs (57) ABSTRACT

The present invention provides a method of using a medical tubing with a pump for administering measured amounts of a beneficial fluid over time to a patient comprising the steps of providing a tubing having a first layer selected from the group consisting of ethylene homopolymers and ethylene copolymers, wherein the copolymers of ethylene are an ethylene monomer copolymerized with at least one monomer selected from the group consisting of lower alkyl olefins, lower alkyl esters of a carboxylic acid, and lower alkene esters of a carboxylic acid, the lower alkyl and lower alkene having from 3 to 18 carbons, the tubing having been exposed to a sterilization dosage of radiation of from about 15 to about 45 kGys; and pumping fluid through the tubing with the pump.

68 Claims, 5 Drawing Sheets

U.S. PATENT DOCUMENTS

| | | |
|---|---|---|
| 2,551,710 | 5/1951 | Slaughter . |
| 3,157,724 | 11/1964 | Salyer et al. . |
| 3,218,380 | 11/1965 | Euling et al. . |
| 3,260,776 | 7/1966 | Lindstrom, Jr. et al. . |
| 3,581,776 | 6/1971 | Sheahan . |
| 3,775,523 | 11/1973 | Haley . |
| 3,856,889 | 12/1974 | McConnell . |
| 3,886,227 | 5/1975 | VanBrederode et al. . |
| 3,974,240 | 8/1976 | Bock et al. . |
| 4,014,369 | 3/1977 | Kobres, Jr. . |
| 4,157,194 | 6/1979 | Takahashi . |
| 4,157,235 | 6/1979 | Lagabe et al. . |
| 4,193,899 | 3/1980 | Brenner et al. . |
| 4,374,882 | 2/1983 | Harlan . |
| 4,422,999 | 12/1983 | Mitchell . |
| 4,444,817 | 4/1984 | Subramanian . |
| 4,479,989 | 10/1984 | Mahal ............................. 428/35.5 |
| 4,563,259 | 1/1986 | Rayner ................... 524/99 |
| 4,613,533 | 9/1986 | Loomis et al. . |
| 4,623,567 | 11/1986 | Hart . |
| 4,678,834 | 7/1987 | Boivin et al. . |
| 4,698,196 | 10/1987 | Fabian . |
| 4,721,637 | 1/1988 | Suzuki . |
| 4,737,547 | 4/1988 | White . |
| 4,886,634 | 12/1989 | Strutzel et al. . |
| 4,906,496 | 3/1990 | Hosono et al. . |
| 4,948,643 | 8/1990 | Mueller . |
| 4,957,974 | 9/1990 | Ilenda et al. . |
| 5,018,945 | 5/1991 | D'Silva . |
| 5,045,620 | 9/1991 | Itaba et al. . |
| 5,047,253 * | 9/1991 | Juhl et al. ............................ 426/113 |
| 5,048,572 | 9/1991 | Levine . |
| 5,151,019 | 9/1992 | Danby et al. . |
| 5,169,708 | 12/1992 | Amaral et al. . |
| 5,225,451 | 7/1993 | Rogers et al. . |
| 5,241,031 | 8/1993 | Mehta . |
| 5,264,488 | 11/1993 | Takeuchi et al. . |
| 5,274,035 | 12/1993 | Chundury . |
| 5,281,670 | 1/1994 | Lee et al. . |
| 5,343,738 | 9/1994 | Skaggs . |
| 5,439,454 | 8/1995 | Le et al. . |
| 5,525,388 | 6/1996 | Ward et al. . |
| 5,562,127 | 10/1996 | Fanselow et al. .................... 138/137 |
| 5,573,822 | 11/1996 | Nishikawa et al. . |
| 5,620,760 | 4/1997 | Galimberti et al. . |
| 5,629,059 | 5/1997 | Desai et al. . |
| 5,638,660 | 6/1997 | Kuo . |
| 5,712,044 * | 1/1998 | Fanselow et al. .................... 428/515 |
| 5,766,744 * | 6/1998 | Fanselow et al. .................... 428/213 |
| 5,932,307 * | 8/1999 | Ryan et al. ......................... 428/36.9 |

FOREIGN PATENT DOCUMENTS

| | | |
|---|---|---|
| 0 133 355 | 7/1984 | (EP) . |
| 0 142 315 | 5/1985 | (EP) . |
| 0 256 644 | 2/1988 | (EP) . |
| 0 450 088 A1 | 10/1991 | (EP) . |
| 0 735 089 A2 | 10/1996 | (EP) . |
| 0 735 089 A3 | 2/1999 | (EP) . |
| 4-332624 | 11/1992 | (JP) . |
| 5-017639 | 1/1993 | (JP) . |
| 7-205275 | 8/1995 | (JP) . |
| 7-205276 | 8/1995 | (JP) . |
| WO 80/02671 | 12/1980 | (WO) . |
| 85/00197 | 5/1985 | (WO) . |
| WO 92/18173 | 10/1992 | (WO) . |
| WO 94/26793 | 11/1994 | (WO) . |
| 95/10706 | 8/1995 | (WO) . |
| WO 96/08520 | 3/1996 | (WO) . |
| WO 96/36374 | 11/1996 | (WO) . |
| 97/07032 | 4/1997 | (WO) . |
| 97/07033 | 4/1997 | (WO) . |
| 97/07034 | 4/1997 | (WO) . |
| 97/07040 | 4/1997 | (WO) . |

* cited by examiner

MEDICAL TUBING AND PUMP PERFORMANCE ENHANCEMENT BY IONIZING RADIATION DURING STERILIZATION

RELATED U.S. APPLICATION DATA

This is continuation-in-part application of U.S. application Ser. No. 08/642,275, filed May 3, 1996, now U.S. Pat. No. 5,932,307, which is incorporated herein and made a part hereof by reference.

TECHNICAL FIELD

This invention relates to a method for fabricating medical tubing and more particularly to a process for improving medical pump tubing performance by irradiating the tubing and optionally by also orienting the tubing.

BACKGROUND ART

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride. These new materials for tubing must have a unique combination of properties, so that the tubing may be used in fluid administration sets and with medical infusion pumps. Among these properties are the materials must be optically clear, environmentally compatible, have sufficient yield strength, elasticity and flexibility, have a minimum quantity of low molecular weight additives and other extractables, and be compatible with medical solutions.

It is desirable for medical tubing to be optically transparent to allow for visual inspection of fluids in the tubing. It is also desirable for the tubing to be optically and ultrasonically transparent as it increases the compatability of the tubing with medical infusion pumps. Medical infusion pumps are equipped with ultrasonic sensors for detecting abnormal conditions in the tubing such as air bubbles.

It is also a requirement that the tubing be environmentally compatible as a great deal of medical tubing is disposed of in landfills and through incineration. For tubing disposed of in landfills, it is desirable to use as little material as possible to fabricate the tubing. Further benefits are realized by using a material which is thermoplastically recyclable so that scrap generated during manufacturing may be incorporated into virgin material and refabricated into other useful articles.

For tubing that is disposed of by incineration, it is necessary to use a material that does not generate or minimizes the formation of by-products such as inorganic acids which may be environmentally harmful, irritating, and corrosive. For example, PVC may generate objectionable amounts of hydrogen chloride (or hydrochloric acid when contacted with water) upon incineration.

To be compatible with medical solutions, it is desirable that the tubing material be free from or have a minimal content of low molecular weight additives such as plasticizers, stabilizers and the like. These components could be extracted by the therapeutic solutions that come into contact with the material. The additives may react with the therapeutic agents or otherwise render the solution ineffective. This is especially troublesome in bio-tech drug formulations where the concentration of the drug is measured in parts per million (ppm), rather than in weight or volume percentages. Even minuscule losses of the bio-tech drug can render the formulation unusable. Because bio-tech formulations can cost several thousand dollars per dose, it is imperative that the tubing material be inert.

Polyvinyl chloride ("PVC") has been widely used to fabricate medical tubing as it meets most of these requirements. PVC tubing is optically clear to allow for visual inspection of the fluid flowing through it. PVC tubing has proven to work well in pump administration sets. PVC medical tubing also has desirable stress-strain characteristics so that the material may be stretched to a certain degree along a longitudinal axis of the tubing without causing a significant permanent reduction in the diameter of the tubing. In other words, PVC tubing resists necking. PVC medical tubing also has favorable surface characteristics to allow for controlling the flow rate of fluid through the tubing using slide clamps which operate by crimping the sidewall of the tubing to stop or reduce the flow of fluid through the tubing. The slide clamp may be used without causing scoring or cutting of the tubing.

Because PVC by itself is a rigid polymer, low molecular weight components known as plasticizers must be added to render PVC flexible. As set forth above, in some instances these plasticizers may be extracted out of the tubing by fluid passing through the tubing. For this reason, and because of the difficulties encountered in incinerating and recycling PVC, there is a desire to replace PVC medical tubing.

Polyolefins and polyolefin alloys have been developed which meet many of the requirements of medical containers and tubing, without the disadvantages associated with PVC. Polyolefins typically are compatible with medical applications because they have minimal extractability to fluids. Most polyolefins are environmentally sound as they do not generate harmful degradants upon incineration, and in most cases are capable of being thermoplastically recycled. Many polyolefins are cost effective materials that may provide an economic alternative to PVC. However, there are many hurdles to overcome to replace all the favorable attributes of PVC with a polyolefin.

For example, problems have been encountered in using certain polyolefins to fabricate medical tubing. Such tubing has been found to have poor surface characteristics so that it is readily susceptible to cutting, shredding or scoring when clamping the tubing using a slide clamp. Certain polyolefin tubing also presents difficulties during use in pump pressurized administration sets where the pump controls the flow rate of fluid through the tubing by consecutively impinging upon the sidewalls of the tubing to deliver a precise amount of fluid over a given time period.

Pumps that are used to infuse beneficial agents to patients typically have various sensors to detect such conditions as back pressure of fluid in the tubing, and air bubbles in the fluid stream. The sensors deactivate the pump upon detecting an unacceptable back pressure or an air bubble. The sensors usually have a sensor body in which a segment of the tubing of the administration set is secured in place. It has been found that there is a tendency for the polyolefin tubing to deform when placed in the sensor body due to resistance with side walls of the sensor housing. This deformation in some cases leads the detectors to indicate an abnormal condition and to inappropriately deactivate the infusion pump.

Further, certain polyolefin tubing has been found to have low yield strength. Because there is a direct relationship between yield strength and modulus, it is very difficult to increase the yield strength without increasing at the same time the modulus of the material. In polyolefin materials, the modulus is primarily dependent on crystallinity. In PVC materials, the modulus is primarily dependent on the amount of plasticizer added. When the modulus of the polyolefin material is selected to match that of the plasticized PVC, the polyolefin material's yield strength becomes significantly reduced, and the resulting tubing has too low a yield strength to resists potentially external pulling forces that can result in necking of the tubing. Conversely, when the yield strength is matched with PVC the resultant modulus is too high to function with pumps.

Polyolefin tubing exhibiting low yield strengths are readily susceptible to a phenomenon which is referred to as necking. Necking is a localized reduction in the diameter of the tubing that occurs upon stretching the tubing under moderate strain along the longitudinal axis of the tubing. Necking can cause a reduction in the flow of fluid through the tubing thereby rendering the tubing ineffective.

Applicants have found that it is possible to increase the tubing's resistance to necking by pre-orienting the tubing along the longitudinal axis of the tubing. However, the orientation process may lead to dimensional instability. In particular, oriented polyolefin tubing experiences a phenomenon known as heat recovery, which is sometimes referred to as the "memory effect." Heat recovery is a complicated phenomenon that occurs when oriented tubing is heated above the temperature reached during the orientation process. When this occurs the tubing loses its orientation causing shrinking and dimensional changes of the tubing.

In addition, Applicants have found that most medical tubings undergo some permanent deformation when subjected to the long term (24 hours), repetitive, cyclic stresses introduced by pumping mechanisms such as Baxter's FLO-GARD® 6000 Series pumps. Over this long term use, the deformation causes a variance in the solution delivery rate from the initial rate. This is especially true for polyolefin tubing with low crystallinity.

Polyolefin tubing have also been shown to have poor thermal stability during storage, transportation, and end applications. The poor thermal stability of polyolefin tubing can lead to changes in the desired dimensions and shape. These dimensional and shape changes can possibly adversely affect the accuracy of fluid volume delivery. It can also lead to shape changes that can render the tubing incompatible or difficult to use with pumps. One such problem occurs when tubing, which is frequently stored and shipped in a coiled state, becomes set in that coiled shape. Such coiled tubing is difficult to use as it has the tendency to return to a coiled shape.

One method of improving the thermal stability of non-PVC, polyolefin materials was contemplated in U.S. Pat. No. 4,465,487 issued to Nakamura et al. and assigned to Terumo Kabushiki Kaisha of Japan ("Nakamura"). Nakamura relates to a container for medical use produced from a polyolefin material. More particularly, Nakamura relates to a medical container produced from an ethylene-vinyl acetate (EVA) copolymer containing 10 to 35 weight percent of vinyl acetate cross-linked using an electron beam supplied at 50 to 200 kGys to achieve an EVA copolymer having a gel content of 50% or more. (Col. 3, lines 40–46). The material is cross-linked so that the container can withstand temperatures reached during steam sterilization. However, the resulting high gel content of the material caused by a high dose of radiation renders the material a thermoset by nature, and thus, the material of the Nakamura container may not be recyclable by conventional means.

Others have provided non-PVC multilayered tubings. For example U.S. Pat. No. 5,562,127 discloses a chlorine-free multilayered tubing material having an inner thermoplastic layer having a Young's modulus from about 2 to about 60 MPa and an outer layer having a Young's modulus of equal to up to about seven times the Young's modulus of the inner layer. (Col. 2, line 33-col. 3, line 8). The outer layer reportedly provides toughness and abrasion resistance. (Col. 2, lines 62–64). However, without special processing conditions the tubing is likely to be too stiff to be compatible with medical infusion pumps such as Baxter's FLO-GARD®.

Therefore, the need exists for medical tubing produced from a polyolefin material having a thermoplastic nature and the desirable characteristics of PVC materials without the elution of plasticizers.

DISCLOSURE OF INVENTION

The present invention provides a method for enhancing the performance of tubing when used in a pump by exposing the tubing to sterilization levels of radiation to improve the elasticity and resiliency of the tubing. The polymeric material used to produce the tubing is given a low level dose of radiation supplied by either an electron beam or cobalt-60 gamma sources during the sterilization process. The radiation dosage is preferably less than 50 kGys on the order of 15 kGys to 45 kGys. Such low level radiation dosages allows one to achieve a low gel content. Thus, the elasticity and resiliency of the tubing are enhanced while the tubing remains a thermoplastic capable of being recycled or reprocessed.

The present invention further provides a method of fabricating tubing providing an optional additional step of orienting the tubing along a longitudinal axis. The tubing can be oriented along the longitudinal axis to reduce the diameter of the tubing to define an oriented diameter, and applying heat to the oriented tubing to heat set the tubing to maintain dimensional stability of the tubing. Preferably the initial diameter is 10%–300% greater than the oriented diameter. Preferably the step of orienting the tubing can be done in a wet or a dry process. Each orienting process shares the steps of extending the tubing between a first puller and a second puller spaced apart by a distance and controlling the relative speeds of the first puller and the second puller so that the rate of pulling of the second puller is greater than that of the first puller to orient the tubing therebetween. In the wet orientation process, the tubing is passed through an aqueous bath during the orientation step and in the dry process the tubing is not.

The present invention further provides for heat setting of the tubing to overcome the memory effect discussed above. The heat setting process includes the step of exposing the tubing to a temperature higher than that which the tubing will normally be exposed during shipping, storage, and use, but below the temperature at which the tubing is fully melted. By exposing the tubing to temperatures above the application temperature, less ordered, lower melting crystals are melted leaving higher melting crystals which will be thermally stable over the application temperature range. Part of the highly oriented macro-molecule chains will also be relaxed at heat setting temperatures resulting in a tubing with good thermal stability.

The heat setting step includes the steps of heating the tubing after the orienting step in a heated aqueous bath. Preferably, the tubing is not oriented during the heating step but is held under sufficient tension to prevent the tubing from sagging. It is also possible to allow the tubing a little slack so the tubing may sag slightly. It is also preferable that the tubing be supported with a structure to prevent or minimize further orienting of the tubing.

In addition, it is desirable to position a plurality of spaced rollers in the heating bath. The tubing is trained about the rollers to define a serpentine pattern so that the tubing makes several lengthwise passes through the heating bath. It may be desirable to motorize these rollers.

The present invention further provides a monolayer tubing of ethylene vinyl acetate copolymer that is exposed to sterilization dosages of radiation to increase pump performance. The present invention also provides a multilayered tubing. In a preferred form the tubing has an outer layer of ethylene vinyl acetate and an inner layer of homopolymers and copolymers of alpha-olefins. Preferably, the modulus of elasticity of the EVA is less than the material of the inner layer.

The multilayered tubing can also have greater than two layers such as three layers. The multilayered tubings will have an outer layer, a core layer and an inner layer. In a preferred form the outer layer is softer than or has a modulus of elasticity less than that of the inner layer.

DETAILED DISCLOSURE

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

I. Radiation Modified Polymeric Medical Tubing

Figures 1, 2, 2A, 3, 3A, 3B:
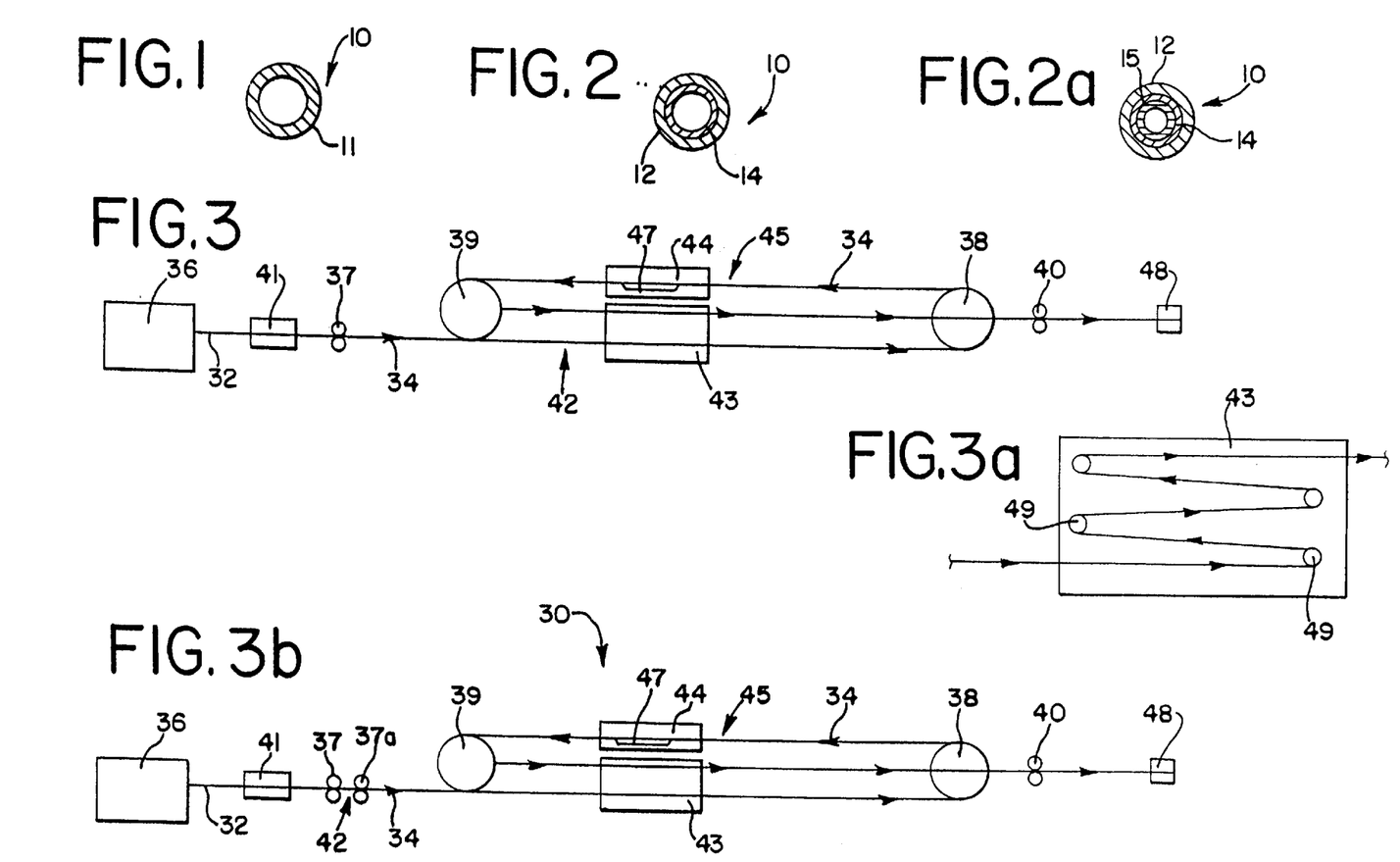
FIG. 1 is an enlarged cross-sectional view of a monolayer medical tubing of the present invention.
FIG. 2 is an enlarged cross-sectional view of a multi-layered tubing of the invention.
FIG. 2a is an enlarged cross-sectional view of a multi-layered tubing of the invention.
FIG. 3 is a schematic representation of a method for forming, orienting and heat setting medical tubing.
FIG. 3a is a plan view of a serpentine pattern that tubing may follow through a heating or cooling bath of the process shown in FIG. 3.
FIG. 3b is a schematic representation of a method for forming, dry orienting and heat setting medical tubing.

FIG. 1 shows tubing structure 10 having a sidewall 12. Preferably the tubing sidewall is fabricated from a polymeric material of an ethylene copolymerized with comonomers selected from the group consisting of lower alkyl olefins, and lower alkyl and lower alkene substituted carboxylic acids and ester and anhydride derivatives thereof. Preferably, the carboxlic acids have from 3–10 carbons. Such carboxylic acids therefore include acetic acid, acrylic acid and butyric acid. The term "lower alkene" and "lower alkyl" is meant to include a carbon chain having from 3–18 carbons more preferably 3–10 and most preferably 3–8 carbons. Preferably, the tubing is an ethylene and vinyl acetate copolymers having a vinyl acetate content of less than about 36% by weight, more preferably less than about 33% by weight and most preferably less than or equal to about 28% by weight. It is also preferred that the EVA have a high molecular weight and a melt flow index as measured by ASTM D-1238 of less than 5.0 g/10 minutes, more preferably less than about 1.0 g/10 minutes and most preferably less than 0.8 g/10 minutes or any range or combination of ranges therein.

It may also be desirable to blend into the tubing material certain amounts of a blending resin of a polyolefin and more particularly homopolymers and copolymers of alpha-olefins. These additives may be blended into the tubing material in an amount from 5% to about 95% by weight of the tubing material. The alpha-olefins may contain from 2 to about 20 carbon atoms or any range or combination of ranges therein. Alpha-olefins containing from 2 to about 10 carbon atoms are more preferred. Thus, the olefin polymers may be derived from olefins such as ethylene, propylene, 1-butene, 1-pentene, 4-methyl-1-pentene, 1-octene, 1-decene, 4-ethyl-1-hexene, etc., or mixtures of two or more of these olefins. Examples of particularly useful olefin polymers include ethylene-butene copolymers and ethylene and propylene copolymers and ethylene and octene-1 copolymers which will be referred to as ultra-low density polyethylenes (ULDPE). Such ULDPE's have a density of preferably equal to or below 0.910 g/cm$^3$ and preferably are produced using metallocene catalyst systems. Such catalysts are said to be "single site" catalysts because they have a single, sterically and electronically equivalent catalyst position as opposed to the Ziegler-Natta type catalysts which are known to have multiple catalysts sites. Such metallocene catalyzed ethylene α-olefins are sold by Dow under the tradename AFFINITY and by Dupont-Dow under the trade name ENGAGE, and by Exxon under the tradename EXACT.

It may be desirable to add a radiation sensitive additive to the tubing material that is responsive to exposure to radiation such as gamma rays, electron beam, ultra-violet light, visible light or other ionizing energy sources. Suitable radiation sensitive additives include organic peroxides such as dicumyl peroxide (DiCup) and other free radical generating compounds. Other free-radical sensitive functional groups include acrylate, acid, dienes and their copolymers and terpolmyers, amide, amine, silane, urethane, hydroyxl, epoxy, ester, pyrolidone, acetate, carbon monoxide, ketone, imidazoline, photo and UV initiators, fluoro-compounds, etc. These functional groups may be in polymeric and non-polymeric compounds. More particularly suitable additives include ethylene vinyl acetate, ethylene methyl acrylate (EMA), ethylene acrylic acid (EAA), fatty amides, low viscosity functionalized and non-functionalized styrene-butadiene copolymers and their hydrogenated derivatives, functionalized and non-functionalized polybutadiene, polyisoprene, ethylene propylene diene monomer terpolymer, polybutene, urethane acrylate, epoxy acrylate, photoinitiators, etc. Even more particularly the additives include low viscosity functionalized ultra-low density polyethylene, functionalized with epoxys, carboxylic acids and their ester and anhydride derivatives, A-C polymers by Allied Signal, SR/CN and Esacure products from Sartomer, functionalized fatty products from Akzo Nobel and Henkel, photoinitiators from Ciba-Geigy, fluoro compounds from 3 M, EVA from DuPont, EAA from Dow Chemical and EMA from Chevron and 1,2-syndiotactic polybutadiene from Japan Synthetic Rubber Co. The ethylene-propylene terpolymers have a third component of a chain nonconjugated diolefin e.g. 1,4-pentadiene, 1,4-hexadiene, 1,5-hexadiene or a cyclic polyene e.g dicyclopentadiene, methylenenorbornene, ethylidenenorbornene, cyclooctadiene, methyltetrahydroindene, etc. These types of additives shall be referred to as EPDM. Suitable EPDM's are sold under the tradenames NORDEL (Dupont Chemical Company), VISTALON (Exxon), KELTAN (Dutch State Mines), JSR (Japan Synthetic Rubber) and EPDM from Mitsui Chemical Company.

The radiation sensitive additives should be added to the tubing material in effective amounts preferably in an amount by weight of the monolayer or outer layer from 0.01–20.0%, more preferably from 0.01–10.0% and most preferably 0.02–5.0%.

Optionally, the tubing material may be further modified by incorporating polar additives to enhance their compatibility with adhesives such as cyanoacrylate type adhesives and improve other surface characteristics such as friction (lubrication). The polar additives preferably are selected from a non-polymeric aliphatic or aromatic hydrocarbon having greater than 5 carbon atoms but less than 500, more preferably less than 200 carbons and most preferably less than 100 carbons in the backbone. Further, the additives should have electron negative groups selected from the group of amines; amides; hydroxyls; acids; acetate, ammonium salts; organometallic compounds such as metal alcoholates, metal carboxylates, and metal complexes of numerous 1,3 dicarbonyl compounds; phenyl phosphines; pyridines; pyrrolidones; imidazoline, and oxazolines. The modification additive can also be a polymer emulsion or solution.

The polar additives should be included in an amount by weight of the tubing material from about 0.001%–10.00%, more preferably 0.01–2.0%.

FIG. 2a shows a multilayered tubing having outer layer 12, inner layer 14 and a core layer 15. In a preferred form, the outer layer 12 and the core layer 15 are constructed of the same material and additives as set forth above for the tubing materials. The outer and core layers 12 and 15 do not have to be of the same material as one another. Preferably the inner layer 14 or solution contact layer is selected from homopolymers and copolymers of alpha olefins. More preferably the inner layer 14 polyolefin is an ethylene copolymer with alpha olefins having from 3–18 carbons and more preferably from 4 to 8 carbons and most preferably is a ULDPE. Preferably, the inner layer has a minimum amount of components that are capable of migrating into a solution passing through the tubing 10. Also, the outer layer 12 should have a modulus of elasticity of less than the inner layer 14. In a preferred form, the core layer 15 will be the thickest layer and constitute from 55–99%, more preferably from 75–99% and most preferably from 90–98% of the total wall thickness or any range or combination of ranges therein.

In a two-layered tubing structure shown in FIG. 2, preferably the outer layer 12 should be thicker than the inner layer 14. Preferably the inner layer will have a thickness in the range of 1–40%, more preferably from 1–25% and most preferably from 2–10% of the total wall thickness or any range or combination of ranges therein.

II. Method of Blending

The components of the polymer blends should be blended through molten mixing, physical blending such as tumble blending, or other means such as reactive extrusion.

III. Method of Fabricating Medical Tubing

The medical tubings 10 of the present invention should have an inner diameter dimension within the range of 0.003–0.4 inches, and an outer diameter dimension within the range of 0.12–0.50 inches. More particularly, medical tubing for use in the administration of fluid using a medical infusion pump, such as Baxter infusion pump sold under the tradename FLO-GARD®, and COLLEAGUE®, have an inner diameter within the range of 0.099–0.105 inches, an outer diameter within the range of 0.134–0.145 inches, and a wall thickness within the range of 0.018–0.021 inches. The tubing should be flexible having a modulus of elasticity of less than 50,000 psi, more preferably less than 30,000, even more preferably less than 10,000 and most preferably less than 4,000 psi, or any range or combination of ranges therein.

IV. Method of Heat Setting and Orienting the Tubing

Optionally, it may also desirable for the tubing 10 to be oriented along its longitudinal axis and set in this dimension using heat. This orientation step increases the yield strength of the tubing in the longitudinal direction thereby reducing the tendency for the tubing to neck during use. In effect, pre-orienting of the tubing increases the resistance to further necking. Preferably, the tubing 10 should be oriented so that the initial inner and outer diameters of the tubing are anywhere from 10%–300% greater than the diameter of the tubing 10 after orienting and more preferably from 20%–120% and most preferably from 30%–100%. These ranges further include all combinations and subcombinations of ranges therein. The ratio of the beginning diameter to the diameter after orienting shall be referred to as the orientation ratio. The orientation process may be a wet orientation process or a dry one as set forth below.

FIG. 3 shows a schematic representation 30 of the method of orienting the tubing 10 in a wet orientation process. The method of wet orienting includes the steps of providing a tubing 10, and orienting the tubing 10 along its longitudinal axis so that the tubing 10 has a desired inner and outer diameter, as specified above in Section III, and orientation ratio. It is believed that the orienting step aligns the molecules of the tubing along the longitudinal axis to increase the resistance to necking upon subsequent longitudinal stressings. The tubing 10 is then heat set to reduce shrinkage of the tubing and to fix the tubing in the oriented dimension.

The tubing 10 (which may be a single layered or multilayered) is pulled in a direction indicated by arrows 34 along a continuous path that may be referred to as a line. The term "up-line" shall refer to locations along the line in a direction opposite the direction to the flow of the tubing 32. Conversely, the term "down-line" shall refer to locations in the direction of the flow of the tubing. By using the term "line" it should not be thought that the method must be carried out in a straight line, rather it should be taken to mean that the method is carried out in a sequence of consecutive steps.

As shown in FIG. 3, tubing 10 is formed with an extruder 36. The tubing 32 exiting the extruder 36 preferably has an outer diameter dimension that will be from 10%–300% greater than after orienting and more preferably from 20%–120%, and most preferably from 30%–100% greater. The tubing 10 is pulled from the extruder 36 with a first puller 37, a second puller 38, a third puller 39, and a fourth puller 40. The diameter of the tubing at the first puller 37, when the tubing is in a solid state, shall be referred to as the initial diameter. The pullers 37, 38, 39 and 40 may have a silicone or rubber coating to increase the coefficient of friction with the tubing 32. The second and third pullers 38 and 39 may have a plurality of axially spaced and circumferentially extending grooves to accommodate more than one set of tubing 32 on a surface of the pullers 38 and 39 at a time.

After exiting the extruder 36, the tubing 32, which is in a molten or semi-molten phase, passes through a first cooling bath 41 where the tubing 32 is cooled with air or a liquid. Preferably, the first cooling bath 41 is a water bath at a temperature within the range of 4° C.–45° C. The tubing should be converted to a solid phase in the cooling bath 41.

After exiting the first cooling bath 41 the tubing 10 extends between the first and second pullers 37 and 38 where the tubing 10 is oriented by operating the second puller 38 at a greater rate of speed than the first puller 37 to achieve the desired orientation ratio. It is believed that orienting the tubing while in the solid state is more effective in achieving an oriented tubing than by stretching the tubing immediately after exiting the extruder 36 or as it is passes through the first cooling bath 41 while the tubing is in a molten or semi-molten phase. This section of the line will be referred to as the orienting section 42. Preferably the second puller 38 is operated at a rate within the range of about 4–10 times faster than the first puller 37. By controlling the relative speeds of the first and second pullers 37 and 38 one can control the final inner and outer diameters of the tubing 10 and achieve the desired orientation ratio.

In the orienting section 42 the tubing 10 is passed through a second cooling bath 43 where the tubing 10 is cooled with air or a liquid. Preferably, the second cooling bath 43, as the first cooling bath 41, is an aqueous bath at a temperature within the range of 4° C.–45° C.

To overcome the memory effect of the oriented tubing 10, it is necessary to heat the tubing to a temperature above that which it will normally be exposed during shipping, storage and use, but below the temperature at which the tubing is fully melted. By exposing the tubing to temperatures above the application temperature, less ordered lower melting crystals are melted leaving higher melting crystals which will be thermally stable over the application temperature range. Part of the highly oriented macro-molecule chains will be relaxed to provide a tubing with enhanced thermal stability.

To this end, after exiting the second cooling bath 43, the tubing 10 trains about the second puller 38 and extends between the second puller 38 and the third puller 39. The tubing 10 proceeds in a direction back toward the extruder 36 and through a heating bath 44 where the tubing is heat set. Preferably, the heat bath 44 is positioned above the second cooling bath 43 to save floor space. However, this positioning is optional. This portion of the process will be referred to as the heat setting section or step 45. Preferably, the heat setting step 45 is done on-line after the orienting section 42, but could be done off-line in a batch mode process. During the heat setting step 45, the tubing 10 is passed through a heating bath 44 where the tubing 10 is heated with a medium such as heated air or liquid. The heating bath 44 preferably is an aqueous solution of water at a temperature of between about 50–99° C. Additives such as salt may be added to the aqueous solution.

In order to control the dimension of the tubing, it is desirable that the tubing 10 not be oriented during the heat setting step 45. For this reason the tubing 10 should be kept under minimum tension to keep the tubing taught or the tubing should be allowed to sag an amount, between the second and third pullers 38 and 39, to prevent or control the shrinkage. Thus, the second and third pullers 38 and 39 should be operated at similar speeds or puller 39 could be operated at a slightly slower speed than puller 38 to accommodate some shrinkage.

To further prevent orienting of the tubing 10 in the heat setting section 45, it may also be desirable to support the tubing 10 while being pulled through the heating bath 44 with a supporting structure 47. However, providing the supporting structure 47 is optional. Suitable supporting structures 47 include a conveyor that moves at the same rate of speed as the tubing 10 through the heating setting section 45. Another supporting structure 47 is a plastic or metal conduit having a diameter greater than that of the tubing wherein the tubing 10 is supported by the interior surface of the conduit.

After exiting the heating bath 44, the tubing 10 extends between the third puller 39 and the fourth puller 40. Puller 40 should be operated at a similar speed of puller 39 or slightly slower than 39 to prevent further orientation. The tubing 10 is passed again through the second cooling bath 43. Of course it is possible to provide for a separate cooling bath, but this arrangement saves floor space.

It may also be desirable to provide for the tubing 10 to make several lengthwise passes through the cooling bath 43 or heating bath 44 as shown in FIG. 3a to provide for maximum cooling or heating of the tubing in a minimal amount of space. This may be accomplished by providing a plurality of spaced rollers 49 to define a serpentine pattern through the heating bath 44 or cooling bath 43.

To prevent any further orientation of the tubing 10, it may be necessary to operate the fourth puller 40 at a similar speed or slightly slower rate of speed than the third puller 39.

After passing the fourth puller 40, the tubing has an oriented diameter and passes through a cutter or spool 48 where the tubing 10 is cut to the appropriate length or wrapped about the spool for storage or shipment.

FIG. 3b shows a dry orientation process 30. The dry orientation process is same in most respects to the wet orientation process with the major exception that the tubing 10 is oriented in section 42 between pullers 37 and 37a. Puller 37a is operated at a speed greater than puller 37. During the dry orientation step 42, the tubing 10 is not submerged in the aqueous bath 43 as is the case in the wet orientation step 42. In the dry orientation process, pullers 38, 39, and 40 will be run at a rate similar to or slower than puller 37a. Notwithstanding these differences between the wet and the dry orientation process, it is desirable that the tubing is oriented while in the solid state.

V. Method of Irradiating the Tubing

Figure 7A:
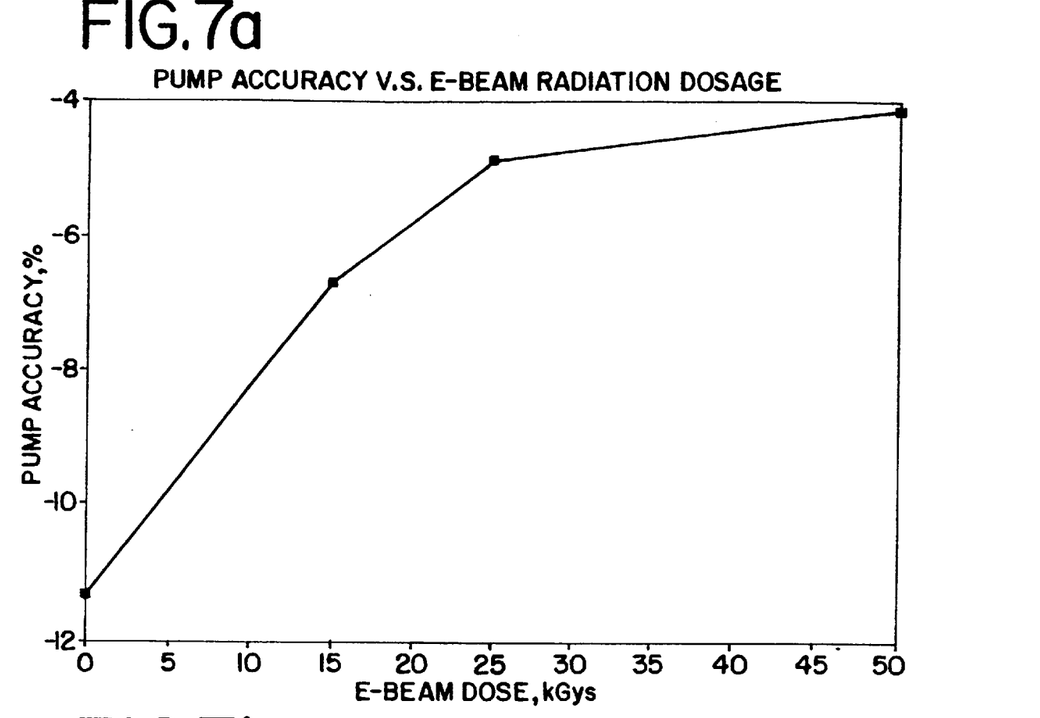
FIG. 7a is a graphical representation of the relationship between pump accuracy and electron beam radiation dosage.
Figure 7B:
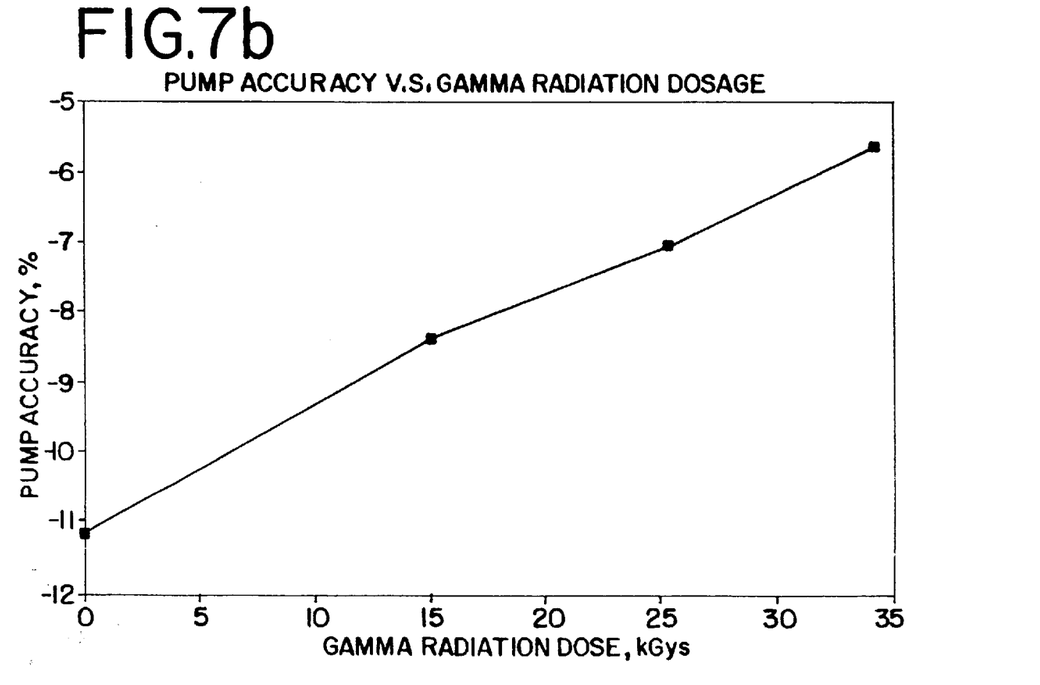
FIG. 7b is a graphical representation of the relationship between pump accuracy and gamma radiation dosage.

During the course of medical device manufacturing, most medical devices have to be sterilized. Radiation sterilization is a preferred method. Surprisingly, it has been found in this investigation that by exposing the tubing to standard sterilization dosages of radiation, the tubing performance as measured by accuracy of fluid dosage delivery was improved. As shown in FIGS. 7a and 7b, pump accuracy increased with increasing dosages of e-beam radiation (FIG. 7a) and gamma radiation (FIG. 7b).

Figure 8A:
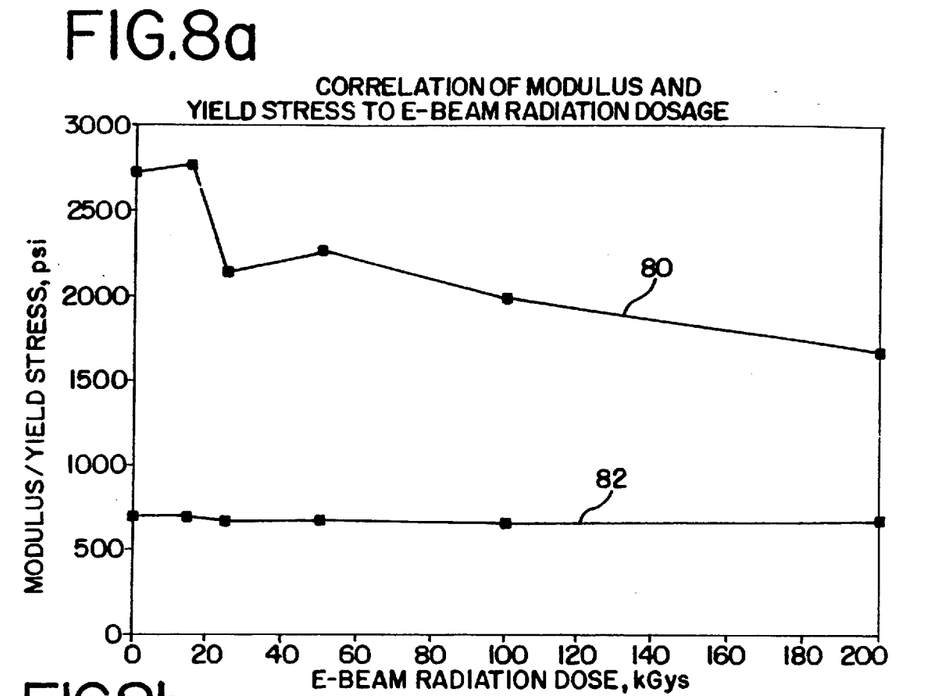
FIG. 8a is a graphical representation of the correlation between modulus of elasticity and yield strength with varying electron beam radiation dosages.
Figure 8B:
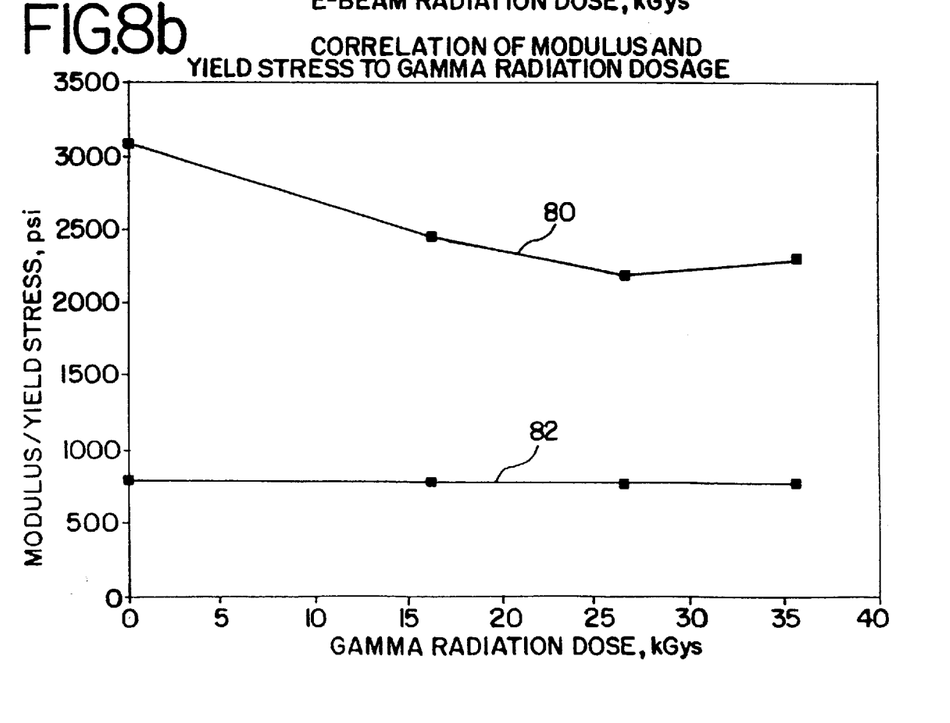
FIG. 8b is a graphical representation of the correlation between modulus of elasticity and yield strength with varying gamma radiation dosages.

As shown in FIGS. 8a and 8b, it was also found that the modulus of elasticity of the tubing, line 80, decreased with increasing dosages of e-beam (FIG. 8a) and gamma radiation dosages (8b). It was surprising that these decreases in modulus were not accompanied by a significant decrease in yield strength of the tubing as indicated by line 82.

Sterilization radiation is typically carried out at much lower doses of radiation than are used to cross-link polymers. The typical magnitude of such sterilization radiation is on the order of about 25 kGys, but can sometimes be as low as 15 kGys.

In some instances, although not necessarily, exposing the tubing to radiation sterilization results in a measurable change in gel content of the tubing. Gel content indicates the percentage of the weight of insolubles to the weight of the tubing material. This definition is based on the well-accepted principle that cross-linked polymer materials are not dissolvable. However, significant gel content such as about 50% renders the material a thermoset. Such thermosets are undesirable for medical usages as they are not capable of recycling using standard recycling techniques.

It is important to note that it is possible to expose tubing to sterilization dosages of radiation and achieve enhanced tubing performance with pumps without observing any changes in the gel content of the tubing. The medical tubing 10 of the present invention exhibits a gel content preferably ranging from 0% to 49.9%, more preferably 0% to 45%, and most preferably 0% to 40%, or any range or combination of ranges therein. Preferably, the tubing is exposed to a low dose of gamma radiation ranging from 15 kGys to 58 kGys, more preferably 15 kGys to 45 kGys, and most preferably 15 kGys to 35 kGys, or any range or combination of ranges therein. Thus, this tubing 10 maintains its thermoplastic characteristics and can be reprocessed or recycled using standard recycling techniques.

Pump accuracy can also be improved after even lower doses of radiation when very minute amounts of the radiation-sensitive additives described above are added to the polymeric material prior to extrusion.

An example of a pump in which an improvement in tubing performance has been observed is the FLO-GARD® 6201. The FLO-GARD® 6201 is a single pump head, electromechanical, positive pressure, peristaltic, intravenous, infusion device. The pump is designed to operate with standard PVC intravenous tubing that conforms to Baxter specifications. The pump has a primary flow rate range from 1 to 1999 mL/hr. The secondary range is 1 to 999 mL/hr, or the upper limit will be the same as the primary rate limit, which ever is lower. Infusible volume for both secondary and primary modes is 1 to 9999 mL. This pump has the capability of operating with a wide variety of standard I.V. administration sets including: basic sets, filter sets, CONTINU-FLO®, and BURETROL® sets. The pump accuracy should be within ±10% for any flow rate setting during 24 hours of continuous service using the same I.V. administration set.

Figure 4:
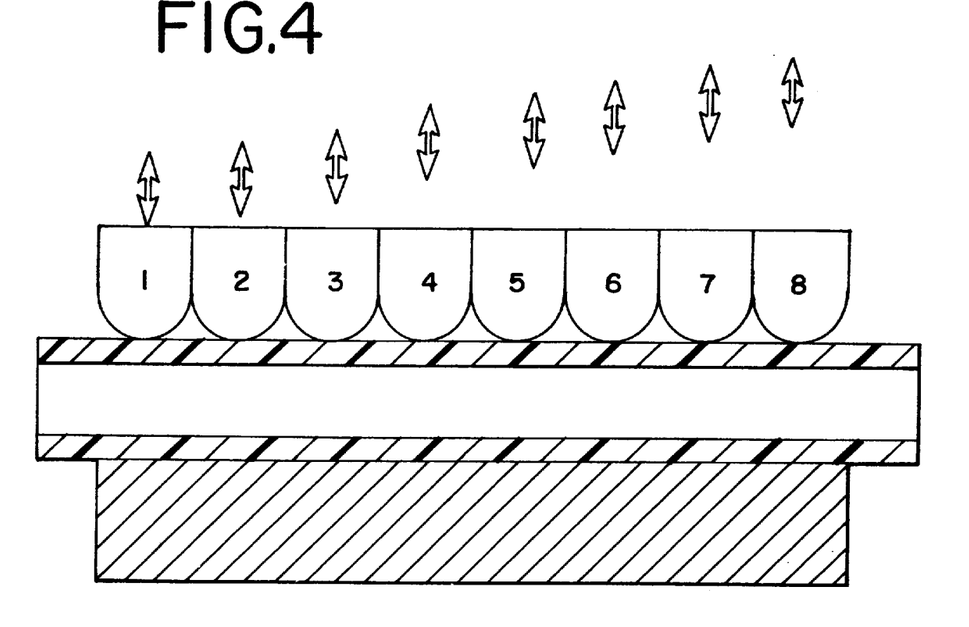
FIG. 4 is a schematic of a method of pumping fluid through polymeric tubing.
Figure 5:
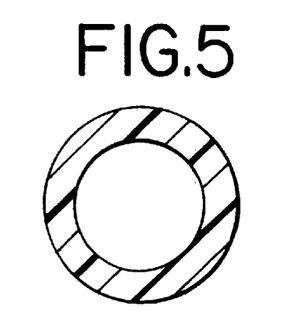
FIG. 5 is a cross sectional view of a polymeric tubing during an up-stroke in a pumping operation.
Figure 5A:
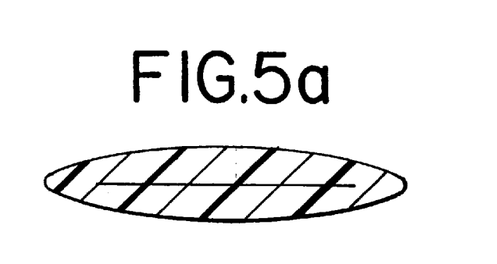
FIG. 5a is a cross-sectional view of a polymeric tubing during a down-stroke in a pumping operation.
Figure 5B:
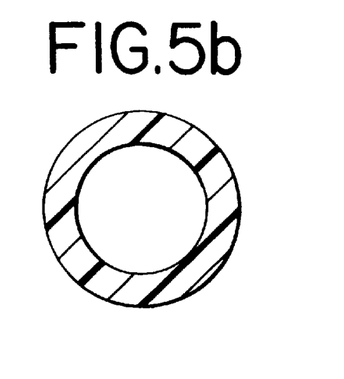
FIG. 5b is a cross-sectional view of a polymeric tubing prior to multiple compressions by a pump.
Figure 5C:
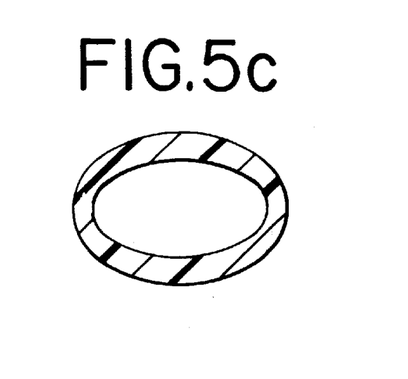
FIG. 5c is a cross-sectional view of a polymeric tubing after multiple compressions with a pump.
Figure 6:
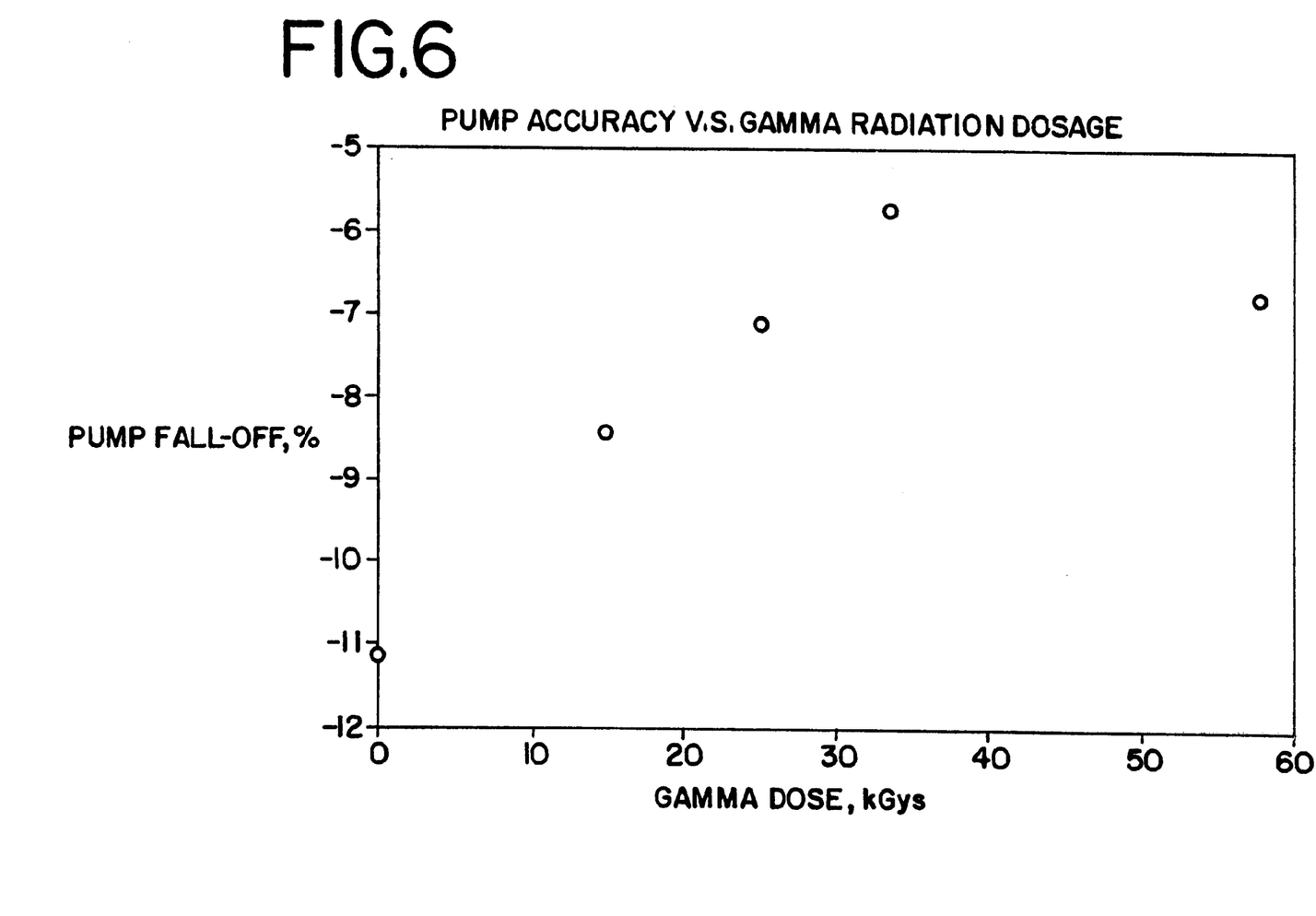
FIG. 6 is a graphical representation of the relationship between pump accuracy and cobalt-60 gamma radiation dosage.

As depicted in FIG. 4, the pump has a series of eight "fingers." The fingers provide positive pressure to squeeze fluid out of the pump segment for delivery to the patient. The eight fingers move up and down in sequence and perform a peristaltic infusion function. During this process, the tubing undergoes repetitive cyclic deformations which eventually may cause permanent deformation in the tubing geometry. (See FIGS. 5b and 5c). This permanent deformation (See FIGS. 6 and 7) leads to a volumetric reduction in the tubing which, in turn, causes an under-delivery of fluid to the patient. Such phenomenon is generally referred to as "pump fall-off."

The Examples below will show that the tubing of the present invention had less change in flow-rate over a 72 hour period when compared to non-radiation sterilized tubing and existing PVC medical tubing.

Illustrative, non-limiting examples of the present tubings are set out below. Numerous other examples can readily be envisioned in light of the guiding principles and teachings contained herein. The examples given herein are intended to illustrate the invention and not in any sense to limit the manner in which the invention can be practiced.

VI. EXAMPLES

Sterilization Radiation Examples

Experiments on fluid delivery accuracy with electromechanical pumps, gel content and relaxation time were conducted to characterize the properties of the irradiated tubing. Gel content was determined by solvent extraction. The tubing samples were extracted by refluxing in a Soxhlet extractor with 150 mesh stainless steel screen and 250 mL of xylene during 6 to 8 hours, sufficient for a complete extraction of soluble polyolefin materials. The residual materials in the screen were dried under vacuum to a constant weight which was used to calculate gel content:

$$\text{Gel\%} = [\text{weight of residual/weight of sample}] \times 100\%$$

Relaxation time (i.e., the time for force to decay to 1/e (36.8%) of initial force under constant strain rate) at elevated temperature is another way to measure Theological and elastic behavior of polymeric materials. The test procedure is described as follows. A Rheometrics Solid Analyser RSA-II is used for the study. Non-PVC tubing (OD about 0.141 inch) is cut into about 1 inch lengths. A two-plates fixture is heated for 20 minutes at about 75° C. before the 1-inch length of tubing is inserted between the two metal disks (about 0.595 inch diameter). The initial gap between the two disks is about the same as the OD of the tubing (i.e., 0.141 inch). The tubing and the plates are then heated at 75° C. for another 5 minutes before compressing tubing at a constant strain. The initial force and force decay are recorded with time. The relaxation time is taken as the point when the force decrease to 1/e or 36.8% of the initial force value. As shown in the following examples, small increases in relaxation time appear to improve pump accuracy.

1. Example 1

Separate tubings fabricated from 100% ethylene vinyl acetate (EVA) (DuPont ELVAX) and a blend of EVA and Ethomeen 0/15 (0.23 by weight) (Akzo Nobel Chemical Company) were irradiated at various levels of radiation. The mode of radiation provided was cobalt-60 gamma. Each length of tubing was then used in conjunction with a Flo-Gard® 6201 medical infusion pump sold by Baxter Healthcare Corporation as described in detail above. The change in flow rate of the pump through the tubing was measured after 72 hours of continuous usage.

The Flo-Gard® 6201 is a single pump head, electromechanical, positive pressure, peristaltic, intravenous, infusion device. The pump is designed to operate with standard PVC intravenous tubing that conforms to Baxter specifications. The pump has a primary flow rate range from 1 to 1999 mL/hr. Infusible volume for both secondary and primary modes is 1 to 9999 mL. This pump is with a capability of operating with a wide variety of standard administration sets including: basic sets, filter sets, Continu-Flo®, and Buretrol® sets. The pump accuracy should be within ±10% for any flow rate setting during 24 hours of continuous service using the same administration set.

As depicted in FIG. 4, the pump has a series of eight "fingers." The fingers provide positive pressure to squeeze fluid out of the pump segment for delivery to the patient. The eight fingers move up and down in sequence and perform a peristaltic infusion function. During this process, the tubing undergoes repetitive cyclic deformations which eventually may cause permanent deformation in the tubing geometry. (See FIGS. 5 and 5a). This permanent deformation (See FIGS. 6 and 6a) leads to a volumetric reduction in the tubing which, in turn, causes an under-delivery of fluid or pump fall-off.

If the material used to make the tubing does not have similar elastic and creep resistance properties as current PVC material, elevated deformation could occur. This elevated deformation of the tubing would cause greater under-delivery from the preset flow rate as compared to PVC tubing.

Pump fall-off generally decreases with increasing levels of cobalt-60 gamma radiation doses. The level of radiation and change in fluid delivery for Example 1 are set forth below in Table 1.

TABLE 1

| Sample Number | Comp. | Cobalt-60 Gamma, kGys | Pump Fall Off % | Within Limit of ± 10% |
|---|---|---|---|---|
| 17-960604A | 100% EVA | 0 | −11.3 | No |
| 17-960919B | EVA/0.23% Ethomeen | 15 | −8.38 | Yes |
| 17-961008C | EVA/0.23% Ethomeen | 25.4 | −7.06 | Yes |
| 17-961212E | 100% EVA | 34.2 | −5.67 | Yes |
| 17-960827A | EVA/0.23% Ethomeen | 58.1 | −6.75 | Yes |

2. Example 2

Separate monolayer tubings manufactured from a blend of 95% EVA and 5% ULDPE and were treated with different amounts of a precompounded additive, dicumyl peroxide (DiCup). The tubings were then irradiated with escalating doses of cobalt-60 gamma radiation. Finally, the tubings were placed in a FLO-GARD® 6201 infusion pump, and the percent change in flow rate delivered through the tubings was measured.

The level of additive, the radiation dosage, and corresponding change in pump performance is set forth below in Table 2.

TABLE 2

| Sample No. | Composition | Cobalt-60 Gamma, kGys | Pump Fall-Off | Within Limit of ± 10% |
|---|---|---|---|---|
| 17-960813E | 95% EVA/5% ULDPE/0.025 DiCup | 25.4 | −6.13 | Yes |
| 17-960813F | 95% EVA/5% ULDPE/0.050 DiCup | 25.4 | −5.32 | Yes |

3. Example 3

In Example 3, tubing manufactured primarily of EVA was irradiated with different doses of radiation provided by electron beam. Table 3 set forth below shows the change in pump accuracy at different levels of electron beam radiation dosage.

TABLE 3

| Sample # | Composition | Electron Beam, kGys | Pump Fall-Off | Within Limit of ± 10% |
|---|---|---|---|---|
| 17-96064A | 100% EVA | 0 | −11.3 | No |
| 17-960828A | EVA/0.23% Ethomeen | 15 | −6.68 | Yes |
| 17-960828A | EVA/0.23% Ethomeen | 25 | −4.86 | Yes |
| 17-960814C | 100% EVA | 50 | −4.14 | Yes |
| 17-960604A | 100% EVA | 100 | −2.95 | Yes |
| 17-960604A | 100% EVA | 200 | −2.26 | Yes |

4. Example 4

In Example 4, tubing manufactured primarily of EVA was irradiated with different doses of radiation provided by Cobalt-60 Gamma radiation. Table 4 set forth below shows the change in pump accuracy at different levels of Cobalt-60 Gamma radiation dosage.

TABLE 4

| Sample Number | Composition | Cobalt-60 Gamma, kGys | Pump Fall Off, % |
|---|---|---|---|
| 17-960604A | 100% EVA | 0 | −11.13 |
| 17-960919B | EVA / 0.23% Ethomeen | 15 | −8.38 |
| 17-961008C | EVA / 0.23% Ethomeen | 25.4 | −7.06 |
| 17-961212E | 100% EVA | 34.2 | −5.67 |
| 17-960827A | EVA / 0.23% Ethomeen | 58.1 | −6.75 |

5. Example 5

In Example 5, the gel content present in tubing manufactured primarily of EVA was measured after the tubing were irradiated at progressively larger doses of cobalt-60 gamma radiation. Gel content increased appreciably above 50 kGys of radiation. At low doses of radiation, it was learned that gel content could be held to imperceptible levels. However, the relaxation time for these tubing samples still increased. Thus, maintaining the tubing as a thermoplastic rather than a thermoset.

TABLE 5

| Sample # | Composition | Cobalt-60 Gamma, kGys | Relaxation time, sec. | Gel Content % |
|---|---|---|---|---|
| 17-960604A | EVA | 0 | 102 | 0 |
| 17-960919B | EVA/0.23% Ethomeen | 15 | 106 | 0 |
| 17-961008C | EVA/0.23% Ethomeen | 25.4 | 116 | 0 |
| 17-961212E | EVA | 34.2 | 130 | 7 |
| 17-960827A | EVA/0.23% Ethomeen | 58.1 | 128 | 38 |

6. Example 6

This example shows that addition of very small amounts of dicumyl peroxide can increase gel content at the same cobalt-60 gamma radiation level. The results are set forth below in Table 6.

TABLE 6

| Sample # | Composition | Cobalt-60 Gamma, kGys | Gel Content % |
|---|---|---|---|
| 17-960813E | 95% EVA/5% ULDPE/0.025% DiCup | 0 | 0.31 |
| 17-960813E | 95% EVA/5% ULDPE/0.025% DiCup | 25.4 | 2 |
| 17-960813E | 95% EVA/5% ULDPE/0.025% DiCup | 58.1 | 50 |

7. Example 7

In Example 7, five samples comprising primarily EVA were irradiated with five different levels of electron beam radiation. The gel content present in each sample was measured subsequent to the radiation sterilization process. Higher gel contents were observed as the radiation dosage increased. Table 7 summarizes the results of the experiment.

TABLE 7

| Sample Number | Composition | Electron Beam, kGys | Gel Content, % |
|---|---|---|---|
| 17-960604A | EVA | 0 | 0 |
| 17-960828A | EVA / 0.23% Ethomeen | 15 | 0.65 |
| 17-960814C | EVA | 50 | 63 |
| 17-960604A | EVA | 100 | 78 |
| 17-960604A | EVA | 200 | 87 |

8. Example 8

In Example 8, relaxation time was measured as a function of cobalt-60 gamma radiation dosage. Here, five tubing samples comprising mainly EVA were irradiated with five different levels of cobalt-60 gamma radiation. The relaxation time was measured for each sample. This experiment revealed that relaxation time can be increased by normal doses of cobalt-60 gamma sterilization radiation. It can be seen as relaxation time increases, pump fall-off deceases, and, therefore, pump accuracy increases. The results of this experiment are set forth in Table 9.

TABLE 9

| Sample Number | Composition | Cobalt-60 Gamma, kGys | Relaxation Time, Sec | Pump Fall Off, % |
|---|---|---|---|---|
| 17-960604A | EVA | 0 | 102 | −11.13 |
| 17-960919B | EVA / 0.23% Ethomeen | 15 | 106 | −8.38 |
| 17-961008C | EVA / 0.23% Ethomeen | 25.4 | 116 | −7.06 |
| 17-961212E | EVA | 34.2 | 130 | −5.67 |
| 17-960827A | EVA / 0.23% Ethomeen | 58.1 | 128 | −6.75 |

9. Example 9

Relaxation time was also measured as a finction of additive level and cobalt-60 radiation dosage. Table 10 shows that the addition of very small amounts of dicumyl peroxide had increased relaxation times as compared to samples having lower levels of dicumyl peroxide after the samples were irradiated with identical doses of cobalt-60 gamma sterilization radiation.

TABLE 10

| Sample # | Composition | Cobalt-60 Gamma, kGys | Relaxation. time, Sec. |
|---|---|---|---|
| 17-960813E | 95% EVA/5% ULDPE/0.025% DiCup | 0 | 119 |
| 17-960813E | 95% EVA/5% ULDPE/0.025% DiCup | 25.4 | 148 |
| 17-960813E | 95% EVA/5% ULDPE/0.025% DiCup | 58.1 | 178 |

10. Example 10

The relationship between relaxation time and increased doses of electron beam radiation is summarized in Table 11. Six tubing samples composed primarily of EVA were irradiated at six increasingly larger doses of electron beam radiation. As the radiation dosage increased, relaxation time increased. The increase in relaxation time associated with the increase in electron beam radiation was much greater than the increase in relaxation time associated with similar levels of cobalt-60 gamma radiation. (See Table 11).

TABLE 11

| Sample Number | Composition | Electron Beam, kGys | Relaxation Time, Sec |
|---|---|---|---|
| 17-960604A | EVA | 0 | 102 |
| 17-960828A | EVA / 0.23% Ethomeen | 15 | 111 |
| 17-960828A | EVA / 0.23% Ethomeen | 25 | 173 |
| 17-960814C | EVA | 50 | 316 |
| 17-960604A | EVA | 100 | 797 |
| 17-960604A | EVA | 200 | 3000 |

Tubings were constructed with the materials set forth in Table 12 and exposed to various dosages of gamma radiation. The modulus of elasticity was measured to determine the effects of radiation on the modulus of elasticity.

The modulus was measured with an Instron 4201 at room temperature (73° F./50% relative humidity) at a speed of 20 in/min with a 2 inch gauge length.

TABLE 12

| Material | Gamma Dosage (KGYS) | Modulus | Yield |
|---|---|---|---|
| EVA CM576 w/ethomeen S-15 | None | 3156 | 760 |
| " | 19.4 | 3080 | 775 |
| " | 28.9 | 2755 | 758 |
| " | 38.9 | 2640 | 752 |
| EVA CM576 w/ethomeen 0–15 | None | 3088 | 791 |
| " | 16.2 | 2460 | 783 |
| " | 26.7 | 2196 | 767 |
| " | 35.7 | 2293 | 764 |

11. Example 11

In Example 11 multilayered tubings were constructed having an outside layer of CM576 (EVA) and an inside layer of SM8250 or SM 8401 (ULDPE). The tubing samples were exposed to various dosages of a Cobalt-60 gamma source as set forth in Tables 13–14. The tubings were tested for their compatibility with Baxter's FLO-GARD® 6201 pump (Table 13). The tubings were also studied to determine the relationship between yield strength and modulus of elasticity with increasing dosages of Cobalt-60 radiation exposure. As shown in Table 14, as the radiation dosage increased the modulus of elasticity of the tubing decreased significantly with only a slight change in the yield strength (See also FIGS. 8a and 8b).

TABLE 13

| Sample | Composition | Cobalt-60 Gamma (kGys) | Sample Size n = | Pump Falloff (% change over time) |
|---|---|---|---|---|
| 17-970821A | CM576/SM8 250 with 15% Ethomeen 0–15 | 0 | 1 | −9.88 |
| 17-970924B | CM576/SM8 401 with 15% Ethomeen 0–15 (heated bath) | 35.1 | 5 | −1.76 |

TABLE 14

| Sample | Composition | Cobalt-60 Gamma (kGys) | Sample size n = | Modulus (psi) | Yield (psi) |
|---|---|---|---|---|---|
| 17-980220B | CM576/SM8401 with 15% Ethomeen 0–15 (heated bath) | 0 | 5 | 3631 | 880 |
| 17-980220B | CM576/SM8401 with 15% Ethomeen 0–15 (heated bath) | 39.8 | 5 | 2937 | 832 |
| 17-980220B | CM576/SM8401 with 15% Ethomeen 0–15 (heated bath) | 48.7 | 5 | 2875 | 823 |

While specific embodiments have been illustrated and described, numerous modifications are possible without departing from the spirit of the invention, and the scope of protection is only limited by the scope of the accompanying claims.

We claim:

1. A method of using a medical tubing with a pump for administering measured amounts of a beneficial fluid over time to a patient comprising the steps of:

providing a tubing having a first layer selected from the group consisting of ethylene homopolymers and ethylene copolymers, wherein the copolymers of ethylene are an ethylene monomer copolymerized with at least one monomer selected from the group consisting of lower alkyl olefins, lower alkyl esters of a carboxylic acid and lower alkene esters of a carboxylic acid, the lower alkyl and lower alkene each have from 3–18 carbons, or blends thereof;

improving fluid delivery accuracy over time of the tubing by exposing the tubing to a sterilization dosage of radiation of from about 15 to about 45 kGys; and pumping fluid through the tubing with the pump.

2. The method of claim 1 wherein the tubing is an ethylene vinyl acetate copolymer having a vinyl acetate content of not more than 36% vinyl acetate by weight of the copolymer.

3. The method of claim 2 wherein the gel content of the ethylene vinyl acetate copolymer is from about 0–49%.

4. The method of claim 2 wherein the ethylene vinyl acetate copolymer has a melt flow index of less than about 5.0 g/10 minutes.

5. The method of claim 2 wherein the ethylene vinyl acetate copolymer has a melt flow index of less than about 1.0 g/10 minutes.

6. The method of claim 2 wherein the ethylene vinyl acetate copolymer has a melt flow index of less than about 0.80 g/10 minutes.

7. The method of claim 1 wherein the step of exposing the tubing to sterilization dosage of radiation comprises the step of exposing the tubing to a source of radiation selected from the group consisting of gamma rays, ultra-violet rays, and electron beam.

8. The method of claim 1 wherein the step of providing a tubing further includes the step of providing a tubing with a second layer concentrically disposed within the first layer of the tubing.

9. The method of claim 8 wherein the second layer has a modulus of elasticity that is greater than the modulus of elasticity of the first layer.

10. The method of claim 9 wherein the second layer is selected from homopolymers and copolymers of alpha-olefins.

11. The method of claim 10 wherein the second layer is an ultra-low density polyethylene.

12. The method of claim 1 wherein the lower alkyl group and the lower alkene group have from 3–10 carbons.

13. The method of claim 1 wherein the first layer of the tubing further comprises a blending resin of a polyolefin or polyolefin copolymers in an amount by weight from 5–95%.

14. The method of claim 13 wherein the blending resin polyolefin copolymer is an ultra-low density polyethylene.

15. The method of claim 1 wherein the step of improving fluid delivery accuracy over time comprises the step of including a radiation sensitive additive to the tubing.

16. The method of claim 15 wherein the radiation sensitive additive is selected from a compound having at least one functional group selected from the group consisting of organic peroxides, acrylates, acids, amides, amines, silanes, urethanes, hydroyxls, epoxys, esters, pyrolidones, acetates, carbon monoxides, ketones, imidazolines, photo initiators, fluoro-compounds, and dienes.

17. The method of claim 16 wherein the radiation sensitive additive is a dicumyl peroxide.

18. The method of claim 16 wherein the compound having diene functional group is an EPDM.

19. The method of claim 16 wherein the diene functional group is a syndiotactic 1,2-polybutadiene.

20. The method of claim 16 wherein the diene functional group is a styrene butadiene block copolymer.

21. The method of claim 1 wherein the pump is a peristaltic pump.

22. A method of using a medical tubing with a pump for administering measured amounts of a beneficial fluid over time to a patient comprising the steps of:
providing a multilayered tubing having a first layer and a second layer, the first layer of an ethylene monomer copolymerized with at least one monomer selected from the group consisting of lower alkyl esters of a carboxylic acid and lower alkene esters of a carboxylic acid, the lower alkyl and the lower alkene each have from 3–10 carbons, the second layer of homopolymers and copolymers of alpha olefins, the second layer being disposed concentrically within the first layer and having a modulus of elasticity greater than a modulus of elasticity of the first layer;
improving fluid delivery accuracy over time of the tubing by exposing the tubing to a sterilization dosage of radiation of from about 15 to 45 kGys; and
pumping fluid through the tubing with the pump.

23. The method of claim 22 wherein the first layer is an ethylene vinyl acetate copolymer.

24. The method of claim 23 wherein the ethylene vinyl acetate copolymer has a melt flow index of less than about 5.0 g/10 minutes.

25. The method of claim 23 wherein the ethylene vinyl acetate copolymer has a melt flow index of less than about 1.0 g/10 minutes.

26. The method of claim 23 wherein the ethylene vinyl acetate copolymer has a melt flow index of less than about 0.80 g/10 minutes.

27. The method of claim 23 wherein the second layer is an ethylene and alpha olefin copolymer wherein the alpha olefin has from 3 to 8 carbons.

28. The method of claim 27 wherein the second layer is an ultra-low density polyethylene.

29. The method of claim 22 wherein the tubing further comprises a third layer.

30. The method of claim 22 wherein the gel content of the ethylene vinyl acetate copolymer is from about 0–49%.

31. The method of claim 22 wherein the step of exposing the tubing to sterilization dosage of radiation comprises the step of exposing the tubing to a source of radiation selected from the group consisting of gamma rays, ultra-violet rays, and electron beam.

32. The method of claim 22 wherein the step of improving fluid delivery accuracy over time comprises the step of including a radiation sensitive additive to the tubing.

33. The method of claim 32 wherein the radiation sensitive additive is selected from a compound having at least one functional group selected from the group consisting of organic peroxides, acrylates, acids, amides, amines, silanes, urethanes, hydroyxls, epoxys, esters, pyrolidones, acetates, carbon monoxides, ketones, imidazolines, photo initiators, fluoro-compounds and dienes.

34. The method of claim 33 wherein the compound having diene functional group is an EPDM.

35. The method of claim 33 wherein the compound having a diene functional group is a syndiotactic 1,2-polybutadiene.

36. The method of claim 33 wherein the compound having a diene functional group is a styrene butadiene block copolymer.

37. A medical tubing for use with a pump for administering measured amounts of a beneficial fluid over time to a patient comprising:
a sidewall of the tubing having a first layer selected from the group consisting of ethylene homopolymers and ethylene copolymers, wherein the ethylene copolymers are ethylene copolymerized with a monomer selected from the group consisting of lower alkyl olefins having from 3–10 carbons, lower alkyl esters of a carboxylic acid, the lower alkyl having from 3–10 carbons, and lower alkene esters of a carboxylic acid, the lower alkene having from 3–10 carbons, the sidewall having a melt flow index of less than about 5.0 g/10 minutes; and
a sterilization dosage of radiation of from about 15 to about 45 kGys transmitted to the tubing.

38. The tubing of claim 37 wherein the first layer is an ethylene vinyl acetate copolymer.

39. The tubing of claim 38 wherein the ethylene vinyl acetate copolymer has a melt flow index of less than about 1.0 g/10 minutes.

40. The tubing of claim 38 wherein the ethylene vinyl acetate copolymer has a melt flow index of less than about 0.80 g/10 minutes.

41. The tubing of claim 37 wherein the tubing further comprises a second layer concentrically disposed within the first layer.

42. The tubing of claim 41 wherein the second layer has a modulus of elasticity that is greater than a modulus of elasticity of the first layer.

43. The tubing of claim 42 wherein the second layer is an ethylene and alpha olefin copolymer wherein the alpha olefin has from 3 to 8 carbons.

44. The tubing of claim 43 wherein the second layer is an ultra-low density polyethylene.

45. The tubing of claim 41 wherein the tubing further comprises a third layer.

46. A medical tubing for use with a pump for administering measured amounts of a beneficial fluid over time to a patient comprising:
providing a tubing having a first layer selected from the group consisting of ethylene homopolymers and ethylene copolymers, wherein the copolymers of ethylene are an ethylene monomer copolymerized with at least one monomer selected from the group consisting of lower alkyl olefins having from 3 to 18 carbons, lower alkyl esters of a carboxylic acid, the lower alkyl having from 3 to 18 carbons, and lower alkene esters of a carboxylic acid, the lower alkene having from 3 to 18 carbons;
a sterilization dosage of radiation of from about 15 kGys to about 45 kGys transmitted to the tubing; and
wherein the tubing is formed by an extrusion process by an extruder, and wherein the tubing is cooled to a solid state to define an initial diameter and then the tubing is stretched in a direction along a longitudinal axis of the tubing to define an oriented diameter that is less than the initial diameter.

47. The tubing of claim 46 wherein the initial diameter is from 10%–300% greater than the oriented diameter.

48. The tubing of claim 46 wherein the initial diameter is from 20%–120% greater than the oriented diameter.

49. The tubing of claim 46 wherein the initial diameter is from 30%–100% greater than the oriented diameter.

50. The tubing of claim 46 wherein the first layer is an ethylene vinyl acetate copolymer.

51. The tubing of claim 50 wherein the ethylene vinyl acetate copolymer has a melt flow index of less than about 5.0 g/10 minutes.

52. The tubing of claim 50 wherein the ethylene vinyl acetate copolymer has a melt flow index of less than about 1.0 g/10 minutes.

53. The tubing of claim 50 wherein the ethylene vinyl acetate copolymer has a melt flow index of less than about 0.80 g/10 minutes.

54. The tubing of claim 50 further comprising a second layer concentrically disposed within the first layer, the second layer having a modulus of elasticity greater than a modulus of elasticity of the first layer.

55. The tubing of claim 54 wherein the second layer is an ethylene and alpha olefin copolymer wherein the alpha olefin has from 3 to 8 carbons.

56. The tubing of claim 55 wherein the second layer is an ultra-low density polyethylene.

57. A method of manufacturing tubing for use with a pump for administering measured amounts of a beneficial fluid over time to a patient, the method comprising the steps of:

proviking a polymeric material selected from the group consisting of ethylene homopolymers and ethylene copolymers, wherein the copolymers of ethylene are an ethylene monomer copolymerized with a monomer selected from the group consisting of lower alkyl olefins having from 3 to 18 carbons, lower alkyl esters of a carboxylic acid, the lower alkyl having from 3 to 18 carbons, and lower alkene esters of a carboxylic acid, the lower alkene having from 3 to 18 carbons, the polymeric material having a melt flow index of less than about 5.0 g/10 minutes;

extruding the polymeric material into a tubing having a first layer with an extruder; and improving fluid delivery accuracy over time of the tubing by exposing the tubing to a sterilization dosage of radiation of from about 15 to about 45 kGys.

58. The method of claim 57 wherein the method further comprises the steps of:

cooling the tubing exiting the extruder to a solid phase to define an initial diameter; and stretching the tubing in a solid phase to define an oriented diameter that is less than the initial diameter.

59. The method of claim 58 wherein the initial diameter is from 10–300% greater than the oriented diameter.

60. The method of claim 57 wherein the polymeric material is an ethylene vinyl acetate copolymer having a vinyl acetate content of not more than 36% vinyl acetate by weight of the copolymer.

61. The method of claim 60 wherein the gel content of the ethylene vinyl acetate copolymer is from about 0–49%.

62. The method of claim 61 wherein the ethylene vinyl acetate copolymer has a melt flow index of less than about 1.0 g/10 minutes.

63. The method of claim 62 wherein the ethylene vinyl acetate copolymer has a melt flow index of less than about 0.80 g/10 minutes.

64. The method of claim 62 wherein the step of exposing the tubing to sterilization dosage of radiation comprises the step of exposing the tubing to a source of radiation selected from the group consisting of gamma rays, ultra-violet rays, and electron beam.

65. The method of claim 57 wherein the step of extruding a tubing having a first layer further includes the step of extruding a tubing having a second layer concentrically disposed within the first layer of the tubing.

66. The method of claim 65 wherein the second layer has a modulus of elasticity that is greater than a modulus of elasticity of the first layer.

67. The method of claim 66 wherein the second layer is selected from homopolymers and copolymers of alpha-olefins.

68. The method of claim 67 wherein the second layer is an ultra-low density polyethylene.

* * * * *